United States Patent
Tsang et al.

(10) Patent No.: US 9,782,306 B2
(45) Date of Patent: Oct. 10, 2017

(54) BODY CONFORMING DISPOSABLE ABSORBENT ARTICLE HAVING LEG WRAPS AND INTERNAL TOPSHEET AND METHOD OF MAKING SAME

(71) Applicant: DSG Technology Holdings Ltd., Tortola (VG)

(72) Inventors: Patrick King Yu Tsang, Hong Kong (CN); Andrew Wright, Chesterfield (GB); Ian Walker, Chesterfield (GB); Edward Kuo-Shu Chang, Camas, WA (US)

(73) Assignee: DSG Technology Holdings Ltd., Kwai Chung, N.T. (HK)

( * ) Notice: Subject to any disclaimer, the term of this patent is extended or adjusted under 35 U.S.C. 154(b) by 0 days.

(21) Appl. No.: 14/320,128

(22) Filed: Jun. 30, 2014

(65) Prior Publication Data
US 2014/0316365 A1    Oct. 23, 2014

Related U.S. Application Data

(63) Continuation of application No. 12/117,739, filed on May 8, 2008, now abandoned.
(Continued)

(51) Int. Cl.
*A61F 13/15* (2006.01)
*A61F 13/20* (2006.01)
(Continued)

(52) U.S. Cl.
CPC ............ *A61F 13/495* (2013.01); *A61F 13/49* (2013.01); *A61F 13/49014* (2013.01);
(Continued)

(58) Field of Classification Search
CPC .............. A61F 13/49; A61F 13/49014; A61F 13/49017; A61F 2013/4518;
(Continued)

(56) References Cited

U.S. PATENT DOCUMENTS

| 3,780,399 A | 12/1973 | Morel |
| 3,814,100 A | 6/1974 | Nystrand et al. |

(Continued)

FOREIGN PATENT DOCUMENTS

| CN | 1131908 | 9/1996 |
| EP | 0329160 A2 | 8/1989 |

(Continued)

OTHER PUBLICATIONS

Opponents Final Written Submission submitted in European Patent No. 1835876 (Application No. 05853498.3), dated Feb. 2, 2017 [4 pages].

(Continued)

*Primary Examiner* — Michelle M Kidwell
(74) *Attorney, Agent, or Firm* — Alberto Q. Amatong, Jr.; Amatong McCoy LLC

(57) ABSTRACT

A secondary internal topsheet and leg wrap structure is provided in a disposable absorbent garment such as a diaper or training pants. The leg wrap structure has a base layer, a top layer, and an elastic construction disposed inbetween. The elastic construction includes a plurality of spaced apart elastic elements that are aligned in a generally in generally parallel relation. The leg wrap structure and secondary topsheet provides for the efficient formation of a reservoir and a plurality of fluid dams each capable of capturing a quantity of fluid to minimize the occurrence of fluid leaks from the absorbent article. Methods of forming such absorbent articles are disclosed.

23 Claims, 18 Drawing Sheets

Related U.S. Application Data

(60) Provisional application No. 60/916,779, filed on May 8, 2007.

(51) Int. Cl.
  *A61F 13/495* (2006.01)
  *A61F 13/49* (2006.01)
  *A61F 13/494* (2006.01)
  *A61F 13/45* (2006.01)

(52) U.S. Cl.
  CPC .. *A61F 13/49017* (2013.01); *A61F 13/49406* (2013.01); *A61F 13/49413* (2013.01); *A61F 2013/1591* (2013.01); *A61F 2013/4518* (2013.01); *A61F 2013/49025* (2013.01); *A61F 2013/49049* (2013.01); *A61F 2013/4951* (2013.01); *Y10T 156/1051* (2015.01)

(58) Field of Classification Search
  CPC .. A61F 2013/49025; A61F 2013/49049; A61F 2013/4951
  USPC ............ 604/385.01, 385.03, 385.24–385.25, 604/385.27, 394, 396
  See application file for complete search history.

(56) References Cited

U.S. PATENT DOCUMENTS

| | | |
|---|---|---|
| 3,860,003 A | 1/1975 | Buell |
| 4,081,301 A | 3/1978 | Buell |
| 4,100,324 A | 7/1978 | Anderson et al. |
| 4,300,562 A | 11/1981 | Pieniak |
| 4,360,021 A | 11/1982 | Stima |
| 4,381,783 A | 5/1983 | Elias |
| 4,397,645 A | 8/1983 | Buell |
| 4,578,071 A | 3/1986 | Buell |
| 4,636,207 A | 1/1987 | Buell |
| 4,646,362 A | 3/1987 | Heran et al. |
| 4,681,579 A | 7/1987 | Toussant et al. |
| 4,704,115 A | 11/1987 | Buell |
| 4,820,577 A | 4/1989 | Morman et al. |
| 4,900,317 A | 2/1990 | Buell |
| 4,909,803 A | 3/1990 | Aziz et al. |
| 4,938,754 A | 7/1990 | Mesek |
| 5,037,412 A | 8/1991 | Tanzer et al. |
| 5,080,658 A | 1/1992 | Igaue et al. |
| 5,085,654 A | 2/1992 | Buell |
| 5,098,423 A | 3/1992 | Pieniak et al. |
| 5,122,407 A | 6/1992 | Yeo et al. |
| 5,281,207 A | 1/1994 | Chmielewski et al. |
| 5,336,552 A | 8/1994 | Strack et al. |
| 5,342,333 A | 8/1994 | Tanzer et al. |
| 5,350,370 A | 9/1994 | Jackson et al. |
| 5,364,380 A | 11/1994 | Tanzer et al. |
| 5,411,497 A | 5/1995 | Tanzer et al. |
| 5,425,725 A | 6/1995 | Tanzer et al. |
| 5,433,715 A | 7/1995 | Tanzer et al. |
| 5,436,066 A | 7/1995 | Chen |
| 5,549,589 A | 8/1996 | Horney et al. |
| 5,562,645 A | 10/1996 | Tanzer et al. |
| 5,593,399 A | 1/1997 | Tanzer et al. |
| 5,650,222 A | 7/1997 | Des Marais et al. |
| 5,653,702 A | 8/1997 | Brohammer et al. |
| 5,662,636 A | 9/1997 | Benjamin et al. |
| 5,690,627 A | 11/1997 | Clear et al. |
| 5,695,486 A | 12/1997 | Broughton et al. |
| 5,749,259 A | 5/1998 | Hamouda et al. |
| 5,782,819 A | 7/1998 | Tanzer et al. |
| 5,788,684 A | 8/1998 | Abuto et al. |
| 5,853,403 A | 12/1998 | Tanzer et al. |
| 5,863,288 A | 1/1999 | Baker |
| 5,904,675 A | 5/1999 | Laux et al. |
| 5,921,975 A | 7/1999 | Suzuki et al. |
| 5,938,650 A | 8/1999 | Baer et al. |
| 5,947,947 A | 9/1999 | Tanzer et al. |
| 6,068,620 A | 5/2000 | Chmielewski |
| 6,093,474 A | 7/2000 | Sironi |
| 6,129,720 A | 10/2000 | Blenke et al. |
| 6,152,906 A | 11/2000 | Faulks et al. |
| 6,162,959 A | 12/2000 | O'Connor |
| 6,177,607 B1 | 1/2001 | Blaney et al. |
| 6,238,379 B1 | 5/2001 | Keuhn et al. |
| 6,241,713 B1 | 6/2001 | Gross et al. |
| 6,245,693 B1 | 6/2001 | Gagliardi et al. |
| 6,258,076 B1 | 7/2001 | Glaug et al. |
| 6,290,686 B1 | 9/2001 | Tanzer |
| 6,329,565 B1 | 12/2001 | Dutkiewicz et al. |
| 6,420,626 B1 | 7/2002 | Erspamer et al. |
| 6,429,350 B1 | 8/2002 | Tanzer et al. |
| 6,448,464 B1 | 9/2002 | Akin et al. |
| 6,491,677 B1 | 12/2002 | Glaug et al. |
| 6,569,137 B2 | 5/2003 | Suzuki et al. |
| 6,570,056 B1 | 5/2003 | Tanzer et al. |
| 6,610,900 B1 | 8/2003 | Tanzer |
| 6,632,209 B1 | 10/2003 | Chmielewski |
| 6,645,407 B2 | 11/2003 | Kellenberger et al. |
| 6,680,423 B1 | 1/2004 | Tanzer |
| 6,702,800 B1 | 3/2004 | Vukos et al. |
| 6,706,030 B1 | 3/2004 | Okuda et al. |
| 6,730,069 B2 | 5/2004 | Tanzer et al. |
| 6,764,478 B2 | 7/2004 | Ashton et al. |
| 6,849,672 B2 | 2/2005 | Mehawej et al. |
| 6,899,776 B2 | 5/2005 | Bahlmann et al. |
| 6,972,011 B2 | 12/2005 | Maeda et al. |
| 2002/0123732 A1 | 9/2002 | Koyama et al. |
| 2002/0173761 A1 | 11/2002 | Roe |
| 2003/0119394 A1 | 6/2003 | Ranganathan et al. |
| 2003/0119402 A1 | 6/2003 | Melius et al. |
| 2003/0120231 A1 | 6/2003 | Wang et al. |
| 2003/0149414 A1 | 8/2003 | Mehawej |
| 2003/0175418 A1 | 9/2003 | Muthiah et al. |
| 2004/0002690 A1 | 1/2004 | Miyamoto |
| 2004/0006323 A1* | 1/2004 | Hall ................ A61F 13/15593 604/385.24 |
| 2004/0015142 A1 | 1/2004 | Johnston et al. |
| 2004/0039363 A1 | 2/2004 | Sugiyama et al. |
| 2004/0059311 A1 | 3/2004 | Minato et al. |
| 2004/0204697 A1 | 10/2004 | Litvay |
| 2004/0236299 A1* | 11/2004 | Tsang ................ A61F 13/15756 604/385.24 |
| 2005/0171499 A1 | 8/2005 | Nigam et al. |
| 2006/0004334 A1 | 1/2006 | Schlinz et al. |
| 2006/0122571 A1* | 6/2006 | Chang ............... A61F 13/15593 604/385.27 |
| 2006/0135931 A1 | 6/2006 | Suzuki et al. |
| 2006/0142727 A1* | 6/2006 | Suzuki ............. A61F 13/49413 604/385.19 |

FOREIGN PATENT DOCUMENTS

| | | |
|---|---|---|
| EP | 0725616 A1 | 8/1996 |
| EP | 0708628 B1 | 4/1997 |
| EP | 0904759 A2 | 3/1999 |
| EP | 1447066 A1 | 8/2004 |
| EP | 1447067 A1 | 8/2004 |
| EP | 1609448 A1 | 12/2005 |
| GB | 2100130 A | 12/1982 |
| WO | 0 516 877 A1 * | 12/1992 ............ A61F 13/15 |
| WO | 9503019 A1 | 2/1995 |
| WO | 2006007185 A1 | 1/2006 |

OTHER PUBLICATIONS

Response to Notice of Opposition (with First Auxiliary Claims) submitted in European Patent No. 1835876 (Application No. 05853498.3), dated Mar. 11, 2016 [30 pages].

Notice of Opposition to a European Patent filed by SCA Hygiene Products AB; filed in EP Patent No. 1835876 (Application No. 05853498.3) dated Jul. 9, 2015 [16 pages].

* cited by examiner

BODY CONFORMING DISPOSABLE ABSORBENT ARTICLE HAVING LEG WRAPS AND INTERNAL TOPSHEET AND METHOD OF MAKING SAME

CROSS-REFERENCE TO RELATED APPLICATIONS

This application is a continuation of U.S. patent application Ser. No. 12/117,739, filed May 8, 2008, which claims priority under 35 U.S.C. 119(e) from provisional U.S. Patent Application No. 60/916,779 filed May 8, 2007, the contents of which all applications are incorporated herein by reference in their entirety.

TECHNICAL FIELD

The present invention relates to absorbent articles such as disposable diapers, and more particularly, to absorbent articles having a unique secondary topsheet and elastic leg wraps capable of forming a reservoir to contain liquid and a plurality of fluid dams further capable of retaining liquid to improve the overall containment characteristics of the absorbent article, especially the containment of loose fecal material.

BACKGROUND OF THE INVENTION

Disposable absorbent articles are worn to contain and absorb urine and fecal exudates. To this end, an absorbent article incorporates certain improved components or structural attributes which function to provide a close, comfortable fit around the user's legs and waist. Such a close fit enhances the containment and leakage prevention capabilities of the absorbent article.

Typical elements of disposal absorbent articles include a liquid-permeable inner layer or topsheet, a liquid-impermeable outer layer or backsheet, and an absorbent core sandwiched between the inner and outer layers. Elasticized barrier leg cuffs, gathering components, and waistbands are often employed to provide leakage prevention by enhancing the fit of the absorbent article about the thighs and waist of the user. For example, elastic members may be positioned longitudinally along the article, generally outboard of the absorbent core to effect a seal around the legs of the user. In addition, several elastic members e.g., in the form of elongated elastic threads or strands may be positioned laterally throughout the waist regions including side waist regions of the disposable absorbent article to allow the article to stretch during use. In this way, the article can stretch to accommodate variations of waist size and leg size of the user, while maintaining a proper fit and leg seal during use.

One function of absorbent articles such as disposable diapers and adult incontinent briefs is to absorb and contain body exudates. Such articles are intended to prevent body exudates from soiling, wetting, or otherwise contaminating clothing or other articles, such as bedding, that come in contact with the wearer. A limitation of such products is leakage out of the leg seals between the absorbent article and the wearer's leg or waist and onto adjacent clothing. This is most evident with loose fecal material which is not easily absorbed by the absorbent article and tends to freely flow on the top surface of the absorbent article.

Contemporary disposable diapers have elasticized leg cuffs to improve both wearing comfort and the ability to contain body exudates. These elasticized leg cuffs prove somewhat effective to prevent wicking and overflow from a fluid laden absorbent article to clothing contacting the edges of the article in that the elasticized leg flaps present a fluid impervious barrier between the edge of the absorbent core and the contacting clothing, and in addition, provide for a sealing action about the legs of the wearer. Despite the effectiveness of such structures, however, body exudates, especially loose fecal material, can leak through the elasticized leg cuffs and soil the wearer's clothing because the diaper does not constrain the free flow of such material nor provide a structure to hold it within the diaper so that as such material flows along the top surface of the topsheet, it tends to work its way past the elasticized leg cuffs.

Thus, it would be beneficial to provide an absorbent article designed to sustain the proper fit of the article around the legs of the wearer. If would be of further benefit to provide an absorbent article having a reduced possibility of leakage at the legs. It would also be beneficial to provide a reservoir that can constrain the flow of fecal material within the absorbent article to reduce the possibility of its leakage. Additionally, it would be of benefit to provide an absorbent article having easy application and/or removal and improved comfort for the wearer.

BRIEF SUMMARY OF THE INVENTION

The present invention relates to a disposable absorbent article, such as a baby diaper or disposable pull-on garment, which includes a pair of elasticized leg wraps and internal secondary topsheet for effectively forming a reservoir within the absorbent article for preventing liquid and/or solid exudate leakage and providing better fit and aesthetic appearance. Embodiments of the present invention provide an absorbent article having improved liquid and exudate containment characteristics.

Embodiment of the present invention includes a novel secondary topsheet that is incorporated into a disposable absorbent article and characterized by a narrowing of the distance between the pair of elasticized leg wraps when compared to the backsheet distance between the pair of elasticized leg wraps. The narrowing between the pair of elasticized leg wraps proximate to the secondary topsheet enhances the fit of the disposable absorbent article around the crotch region of the user. In particular, the difference between a topsheet gap and a backsheet gap allows the formation of a bucketing/reservoir effect. Different embodiments of this aspect of the invention are contemplated wherein the coversheet or topsheet(s) can be the primary or a secondary (i.e., additional) topsheet, be with or without holes or slits, be of full-length or partial length, be of a width that is less than, equal to or greater than the backsheet width, or be partially or fully glued down to itself to form a topsheet gap allowing the formation of the bucketing/reservoir effect. The details of these and other embodiments are described in the ensuing detailed description.

In one aspect of the present invention, a disposable absorbent article has a central body and a pair of elasticized leg wraps. The central body includes an absorbent core and, thus, may be referred to herein as a central absorbent assembly. When disposed in a generally flat, open condition, e.g., before being worn by a user or at a later stage in the manufacturing process, the central body has or is otherwise further characterized by a front longitudinal edge, a rear longitudinal edge opposite the front longitudinal edge, and a longitudinal centerline extending across the front and rear edges. These front and rear edges define, at least partially, front and rear waist portions, respectively, of the disposable absorbent article. The pair of elasticized leg wraps extends longitudinally adjacent opposite lateral sides of the central body. Each leg wrap is spaced outwardly from the lateral edge of the absorbent core.

In another aspect of the invention, leg wraps incorporated with or into the inventive disposable absorbent article may be characterized by an elastic stretch property or elasticity in the longitudinal direction. This elasticity is imparted to the leg wrap by an arrangement of elastic elements extending longitudinally along the disposable absorbent article. The elasticity of the leg wraps enhances the fit of the disposable absorbent article around the thighs of the user. In a particular embodiment, the elastic elements are parallel and spaced apart from each other, for example, by at least a few millimeters. In a preferred embodiment of the invention, the leg wrap provides an effective sealing function e.g., of a barrier leg cuff and leg gathers and fit function, for the disposable absorbent article.

In yet another aspect of the invention, a method of manufacturing a disposable absorbent article is provided. The method includes providing a central body assembly that includes an absorbent core and a topsheet spanning a topsheet gap and a pair of elasticized leg wraps defined, for example, by a top layer, a bottom layer and a plurality of elastic elements between the top and bottom layers.

It is a further object of the present invention to provide an absorbent article having an internal secondary topsheet and improved elasticized leg wraps defining a plurality of fluid dams so as to provide a dual restraint against the lateral flow of body exudates, thereby improving the containment characteristics of the absorbent article, especially in regard to loose fecal material.

Still other embodiments of the inventive disposable article and their manufacturing methods will become readily apparent to those skilled in the relevant art from the following detailed description of the drawings, wherein the various embodiments of the invention are described by way of illustrating the best mode contemplated for carrying out the invention. The invention is capable of other and different embodiments, its several details are capable of modification and its several structural or processed details are capable of modification in various and obvious respects, all without departing from the spirit and the scope of the present invention. Accordingly, the following drawings and detailed description of the drawings are to be regarded as illustrative in nature and not restrictive.

DETAILED DESCRIPTION OF THE INVENTION

Figure 1:
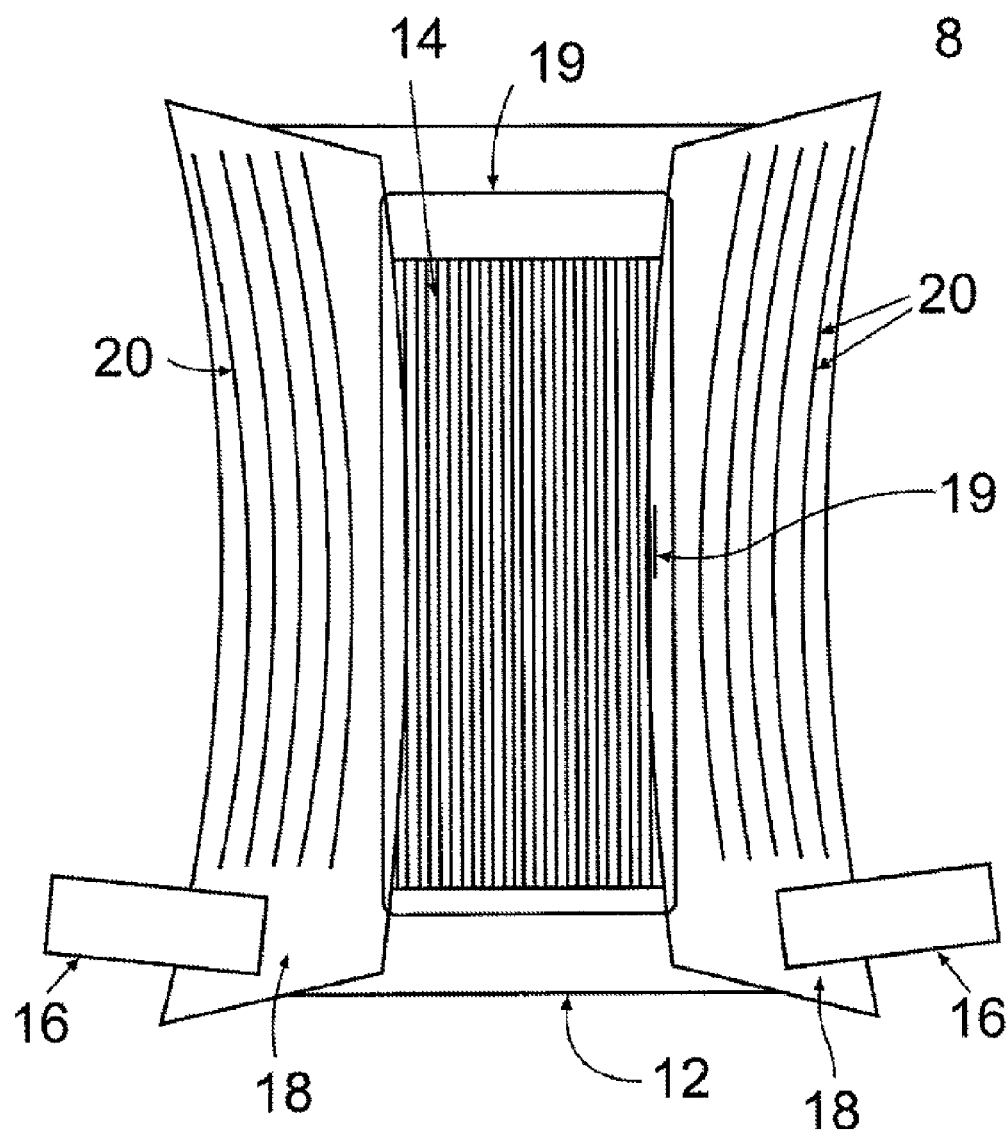
FIG. 1 is a plan view of an inside face of a disposable absorbent article according to the present invention.

As used herein, the term "disposable absorbent article" refers to articles which absorb and contain body exudates and more specifically refers to articles which are placed against or in proximity to the body of the wearer to absorb and contain the various exudates discharged from the body, and to articles which are intended to be discarded after a single use (i.e., they are not intended to be laundered or otherwise restored or reused). A preferred embodiment of the disposable absorbent article of the present invention, as indicated by numeral 8, is shown in FIG. 1. As used herein, the term "absorbent article" refers to a garment generally worn by infants and incontinent persons, which is worn about the lower torso of the wearer. It should be understood, however, that the present invention is also applicable for use in other disposable absorbent articles such as incontinent briefs and the like.

Figure 28:
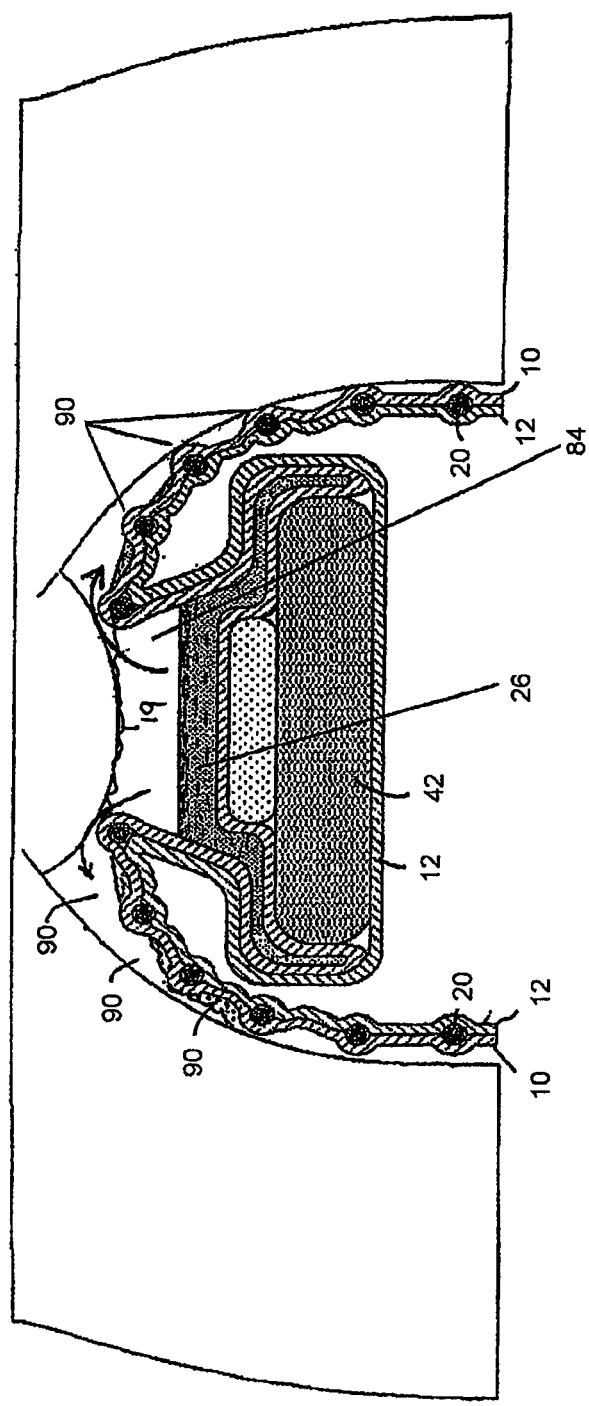
FIG. 28 is a depiction of the absorbent article upon a wearer.

FIG. 1 is a plan view of an absorbent article 8. The absorbent article 8 comprises a liquid pervious topsheet or coverstock 10; a liquid impervious backsheet 12, an absorbent core assembly 14 disposed, for example, between the coverstock 10 and the backsheet 12; a pair of fasteners 16; flexible elastic leg wraps 18; internal topsheet 19; and elastic members 20 secured within the leg wraps 18 and capable of defining a plurality of fluid dams 90 when worn (as shown in FIG. 28). The liquid pervious coverstock 10, absorbent core 14, topsheet 19 and liquid impervious backsheet 12 may be assembled in a variety of well known configurations as appreciated by those of ordinary skill in the art.

Figure 2:
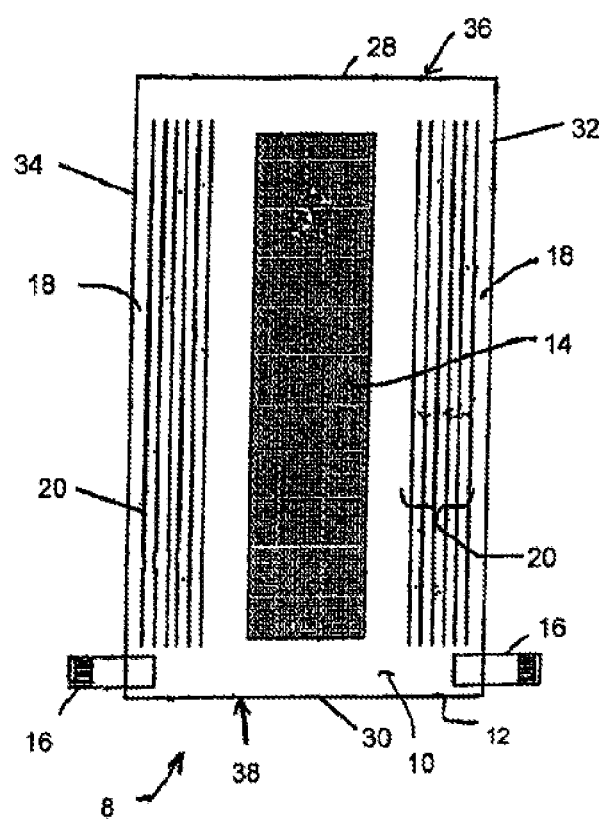
FIG. 2 is a plan view of an inside face of a portion of the disposable absorbent article of FIG. 1 in a generally flat, open condition.
Figure 3:
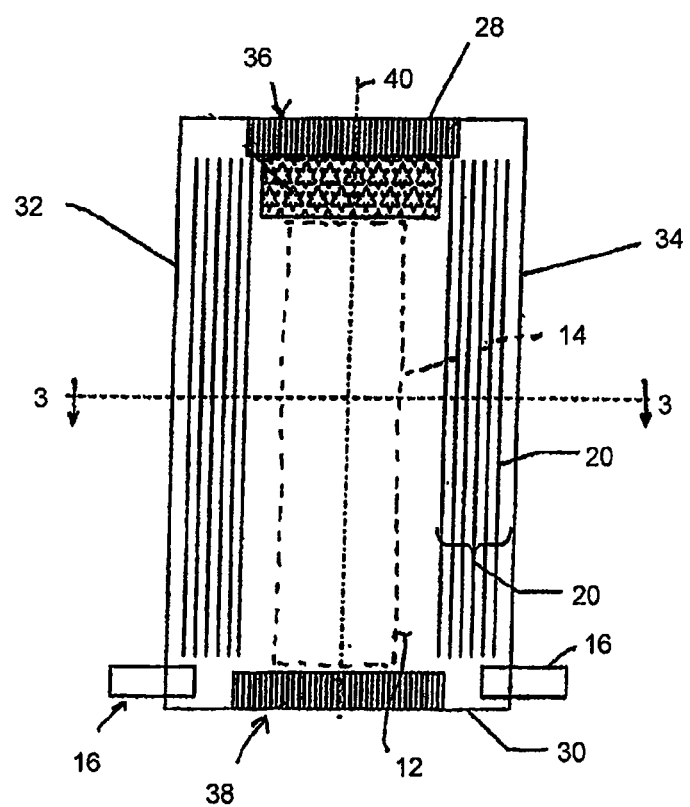
FIG. 3 is a plan view of the outside face of the disposable absorbent article of FIG. 2.

FIGS. 2 and 3 are plan views of the absorbent article 8 of the present invention in the flat-out, uncontracted state (i.e., with all elastic induced contraction removed and prior to any folding operation performed on the article or addition of secondary topsheet 19). The novel secondary topsheet 19 is not shown in FIGS. 2-24. FIG. 3 is a plan view of the other side (outer side) of absorbent article 8 of FIG. 2.

Referring to FIGS. 2 and 3, the absorbent article 8 comprises a liquid pervious topsheet or coverstock 10; a liquid impervious backsheet 12, an absorbent core assembly 14 disposed, for example, between the coverstock 10 and the backsheet 12; a pair of fasteners 16; flexible elastic leg wraps 18; elastic members 20 secured within the leg wraps 18 and capable of defining a plurality of fluid dams 90 when worn (as shown in FIG. 28). The liquid pervious coverstock 10, absorbent core 14 and liquid impervious backsheet 12 may be assembled in a variety of well known configurations as appreciated by those of ordinary skill in the art.

FIGS. 2 and 3 illustrate an embodiment of the absorbent article 8 in which the coverstock 10 and the backsheet 12 are coextensive and have length and width dimension generally larger than those of the absorbent core assembly 14. The coverstock 10 is superposed on the backsheet 12 thereby forming a periphery of the absorbent article 8 comprising end edges 28 and 30, and longitudinal edges 32 and 34.

The absorbent article 8 has waist regions 36 and 38 extending, respectively, from the end edges 28 and 30, of the absorbent article periphery toward the lateral centerline 40 of the absorbent article 8 a distance of from about ¼ to about ⅓ the length of absorbent article 8. The waist regions 36 and 38 comprise those portions of the absorbent article 8 which, when worn, is positioned between the legs of the wearer and covers the lower torso of the wearer.

Figure 4:
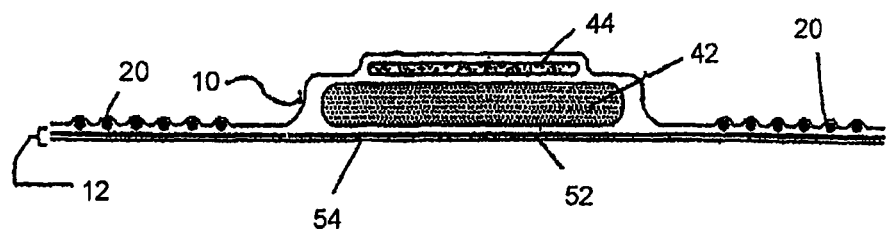
FIG. 4 is a cross-sectional view of the article of FIGS. 2 and 3 along axis 3-3.

Referring to FIG. 4, the absorbent core assembly 14 includes an absorbent core 42, a liquid permeable nonwoven coverstock 10 and a liquid impermeable backsheet 12. Additional layers of a material, such as additional absorbents, cellulose materials or nonwoven 44, that provide additional functionality such as storage of urine, fast acquisition of urine and/or distribution of urine, may also be provided within the core assembly. The absorbent core 42 may be composed of combinations of cellulose based absorbent materials, super-absorbent polymers, synthetic nonwoven materials or other absorbent materials. The disposable, absorbent article 8 is joined together in such a way that the coverstock 10 and backsheet materials 12 entirely enclose the absorbent core 42. The coverstock 10 and backsheet 12 may be directly joined together or indirectly joined together through an intermediate portion. Materials suitable for each of the core 42, coverstock 10 and backsheet 12 are generally known in the art.

The nonwoven coverstock 10 provides a fluid permeable upper layer of the absorbent core assembly to contain the absorbent core components and allows the passage of body exudates into the absorbent core 42 during use. Preferably coverstock 10 has length and width dimensions greater than that of the absorbent core assembly 42. These extended side edges of a nonwoven coverstock 10 may extend to the lateral edges 32, 34 of the absorbent article and serve to provide the upper layer of the composite containing the elastic members 20. The lateral sides of a nonwoven coverstock 10, which extend over the elastic leg wraps 18, may or may not be permeable to aqueous fluids.

The coverstock 10 is preferably compliant, soft feeling, and non-irritating to the wearer's skin. Further, the coverstock 10 is liquid pervious permitting liquids to readily penetrate through its thickness. A suitable coverstock may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from fluids in the absorbent core 42.

A further embodiment of an absorbent article involves the use of a coverstock with zones of differing hydrophilic nature achieved by selective treatment of the material with agents which impart a hydrophilic nature to the nonwoven, e.g. surfactants. In this embodiment the coverstock will have a hydrophilic zone in the centre of the sheet, this central zone aligned to correspond with the region of the article where the absorbent core is disposed. The side zones, laterally adjacent to this central zone, may be less hydrophilic or more hydrophobic than the central zone. This produces an article having a hydrophilic, water permeable coverstock above the absorbent core to allow passage of urine into the core, and hydrophobic, water impermeable regions of said coverstock above the leg gathers to provide a dry feeling around the legs and to resist leakage of fluid through the leg wraps 18.

Leg wraps 18 may include multiple elastic strands 20 associated with each side leg panel 18. In one embodiment, elastic strands 20 are sandwiched between the nonwoven coverstock 10 and the backsheet laminate 12. The composite of the elastic strands 20, nonwoven coverstock 10 and backsheet laminate 12 is secured by using any suitable means familiar to those skilled in the art, such as adhesive bonding using slot coat or spray, spiral or swirl application of hot melt adhesive or ultrasonic bonding. In one embodiment six elastic strands 20 are shown per side leg panel 18. The elastic strands 20 could be yarns of natural or synthetic rubber latex, or synthetic elastic materials such as spandex. The choice of elastic materials is not limited to elastic strands, but may also include ribbons of elastic materials, elastomeric films, elastic scrims, elastic and nonwoven composites and the like.

FIG. 4 is a cross-sectional view of the embodiment of FIG. 2 and FIG. 3 wherein the backsheet material 12 is represented as a laminate of an air porous or air non-porous, fluid impermeable, polyethylene or polypropylene film 52 and a fluid impermeable polypropylene nonwoven 54. Such materials are known to those skilled in the art as clothlike or textile backsheet. It is also suggested that the backsheet material 12 can be a single layer of polyethylene film or other suitable composite material.

The fasteners 16 may involve pressure sensitive adhesive fastening tapes which secure to a frontal portion of silicone, "release" coated polyolefin film, hook and loop tapes or any other suitable fastening medium. The absorbent article may also have an elasticized waistband using an elastic foam, elastic film, elastic strands or other suitable elastic, elastic laminate, stretchable material affixed to or between the coverstock and backsheet portions.

An example of the disposable absorbent article according to the present invention provides a close fitting seal around the thighs of the user, thereby significantly improving its leakage prevention capability. The close fitting seal of the inventive garment is further enhanced through addition of fastening element 16. The fastening element 16 may be provided by known adhesive elements or hook fastening devices. The hook fastening element may be selected so as to be engageable with the loops formed on the surface of a nonwoven fabric. Thus, the nonwoven material of the stretchband panel provides the loop element of a hook and loop fastening system similar to those generally known in the art.

In further embodiments, a loop landing tape may be located near the front waist region of the outside face of the inventive article, and a pair of hook fastening elements may be located in the rear non-elasticized zones of each stretch panel. The fastening portion is therefore attached directly to the central body rather than to the front edge of the stretch panel. The loop landing tape may be constructed from a knitted, extruded, or non-woven material, as is generally known in the art.

Figure 5:
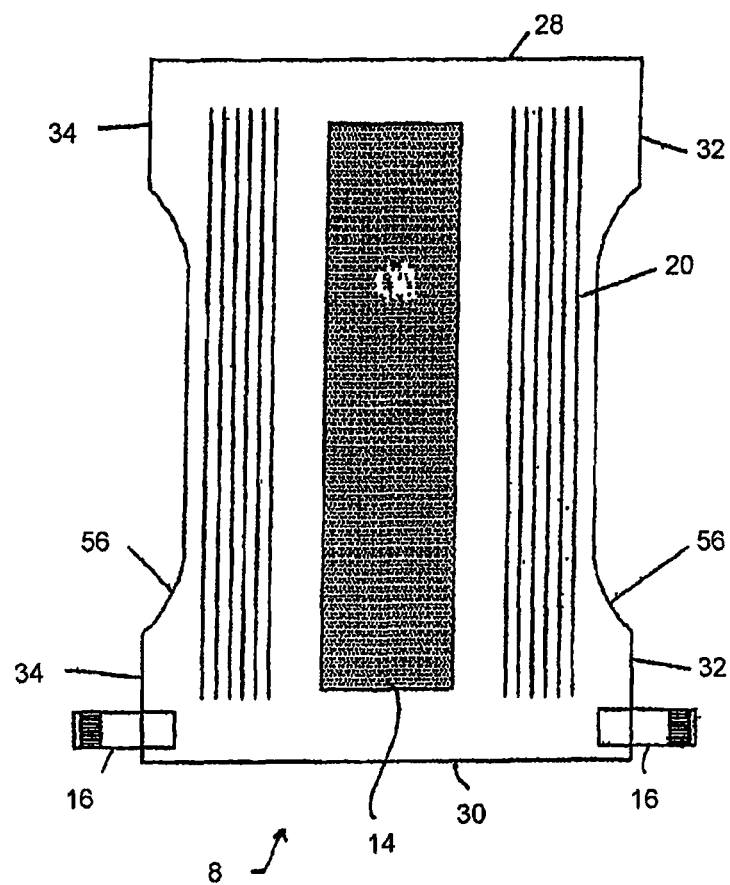
FIGS. 5 and 6 are alternate embodiments of an absorbent article in accordance with the present invention.
Figure 6:
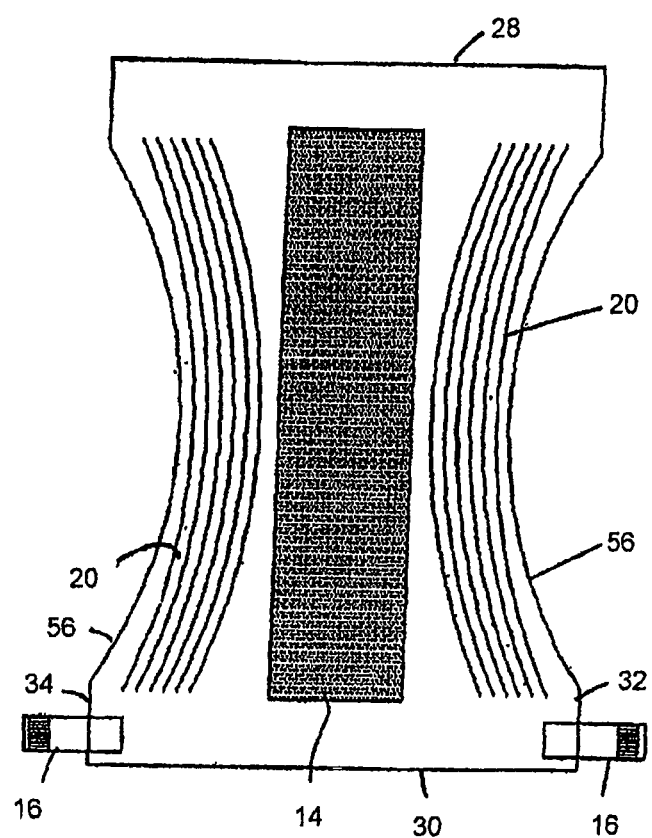

FIGS. 5 and 6 show various other embodiments of absorbent articles 8. FIG. 5 shows an alternative embodiment where the lateral side edges 32, 34 of the absorbent article 8 are inwardly curved to define cut-out regions 56. This shaped product facilitates a better fit of the product around the waist of the wearer without increasing the amount of material within the side panel that would be gathered around the user's legs when worn.

FIG. 5 discloses elastic elements 20 which are oriented parallel to at least a portion of the lateral side edges 32, 34 of the absorbent article 8. In comparison, FIG. 6 depicts elastic elements 20 which follow the inwardly curved side portions of the absorbent article. Descriptions of some additional configurations suitable for use with the present invention are found in U.S. Ser. No. 11/295,781, entitled "Disposable Absorbent Article Having Leg Wraps and Method of Making Same", hereby incorporated by reference and made a part of the present disclosure.

Additional concepts of the present are disclosed in FIG. 6 wherein the absorbent article 8 is defined by a central absorbent core assembly 14 and a pair of leg wraps 18 separated from the absorbent core assembly 14 by inelastic regions or zones 58 of substantially decreased elasticity 58. Each inelastic zone 58 is defined between the absorbent core assembly 14 and the nearest elastic strand member 20 of the leg wraps 18.

Figure 7:
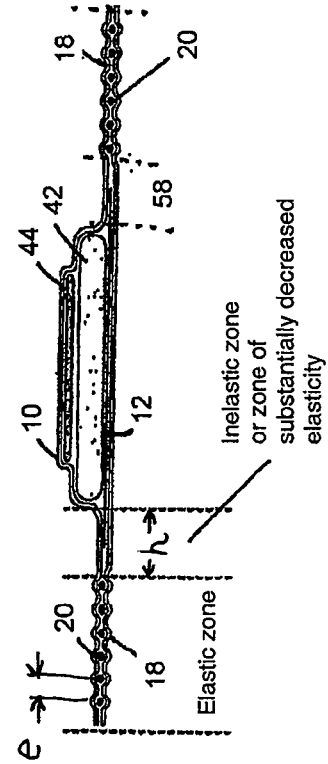
FIG. 7 is a cross sectional view of an absorbent article according to the present invention.

Referring to FIG. 7, a distance, h, is defined between the lateral edges of the absorbent core assembly 14 and the elastic strand 20 nearest to the core assembly 14 or stated another way, the strand 20 furthest from the lateral edges 32, 34 of the absorbent article 8. The spacing between the strands 20 of elastic material is represented as distance, e.

Figure 8:
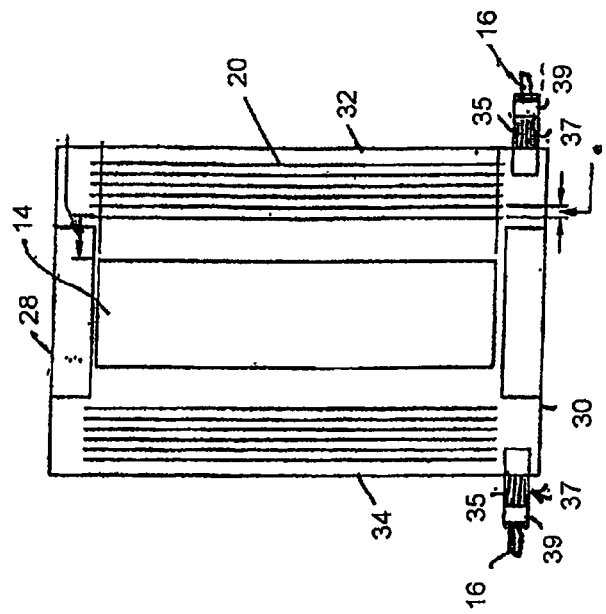
FIG. 8 is a plan view of an absorbent article of an embodiment of the present invention.

FIG. 8 also illustrates another embodiment of the fasteners 16 which may be utilized in the practice of the invention. Fasteners 16 may be provided on the outward portion of side panels 35 having one or more regions of elasticity 37 and one or more regions of inelasticity 39. Other fasteners and side panel constructions are disclosed in U.S. Ser. No. 11/113,114, entitled "Extensible Side Panels For Use With Convertible Absorbent Articles", hereby incorporated by reference and made a part of the present disclosure.

In preferred embodiments of the present invention, the strand 20 count for each elastic leg wrap 18 ranges from 4 to 10 strands, and more preferably between 4 to 6 strands. The distance, h, (width of inelastic zone 58) is preferably between 19 mm to 64 mm, and more preferably between 25 mm to 40 mm. The distance, e, between the strands 20 is preferably between 4 mm to 40 mm, more preferably greater than 6 mm, and yet more preferably approximately 8 mm.

Leg cuff elements 64 may be provided upon a top surface of the coverstock 10 of an absorbent article 8. Leg cuff elements 64 may be defined by material of the coverstock layer 10, or may be of different material attached in know manners to the top surface. The construction of leg cuff elements 64 within the absorbent article 8 would be understood by those of ordinary skill in the art. As depicted in FIGS. 9-13, leg cuff elements 64 may be provided at different distances away from absorbent core 14.

Figure 9:
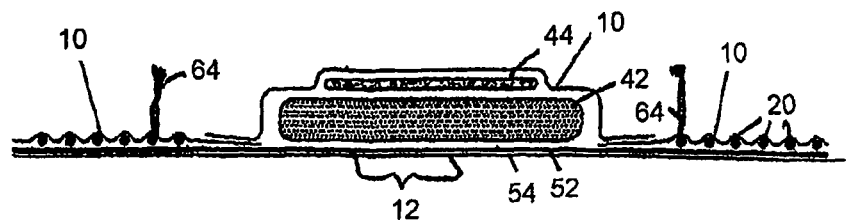
FIGS. 9 to 24 are cross-sectional views of various embodiments of absorbent articles similar to FIGS. 2 and 3.
Figure 10:
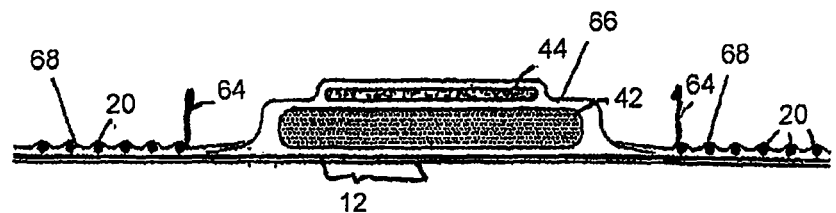

FIGS. 9-24 show cross sections of alternate embodiments of the topsheet, backsheet and absorbent article suitable for use with the internal topsheet 19 (not shown). In some embodiments, the continuous full width nonwoven coverstock 10 may be replaced with a three-piece construction. In the central region 10 of the absorbent article a material 66 permeable to aqueous fluids such as a hydrophilic treated polypropylene nonwoven is placed over the absorbent core to contain the absorbent materials and to allow the passage of urine into the absorbent core 14. Another material element 68 forms the top layer of the elastic side panels 18 along each lateral side edge of the article. This material may be selected from suitable materials such as water permeable polypropylene nonwovens, water impermeable polypropylene nonwovens, polyethylene film and the like. FIG. 9 shows the absorbent core covering material 66 overlapping the outer elastic composite covering material 68. FIG. 10 shows the absorbent core covering material 66 under-lapping the material 68 covering the elastic composite.

Figure 11:
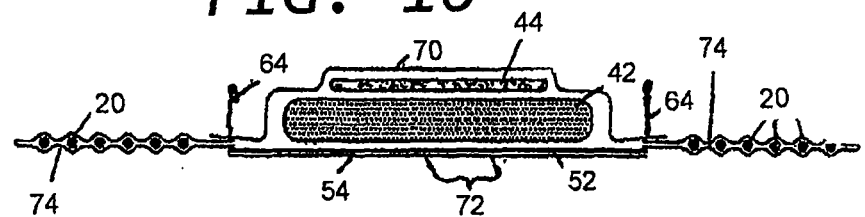

In the embodiment of FIG. 11, an absorbent core assembly 42 is enclosed by a nonwoven, fluid permeable coverstock 70 and a fluid impermeable backsheet 72. In this embodiment the coverstock 70 and backsheet 72 do not extend to the outer edges of the absorbent article. A single ply of nonwoven web 74 is folded around and encloses the elastic strands 20. This elastic composite is then attached to the sides of the absorbent core assembly 14 using any suitable means, for example using hotmelt adhesives or ultrasonic bonding.

Figure 12:
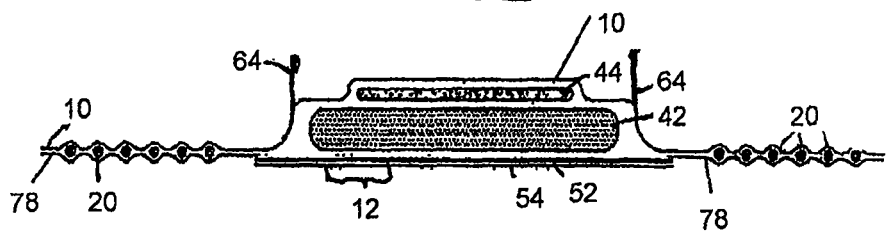

In the example of FIG. 12, the coverstock material 10 extends continuously over the full width of the absorbent article 8, as is the case in the first embodiment of the invention. In this embodiment a separate piece of suitable material 78 is used to enclose the underside of elastic composite on each leg wrap 18.

Figure 13:
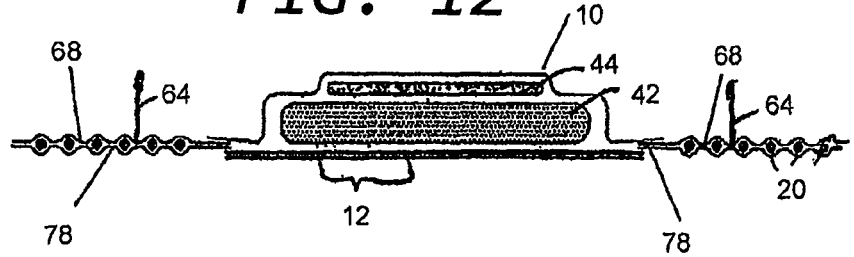
Figure 14:
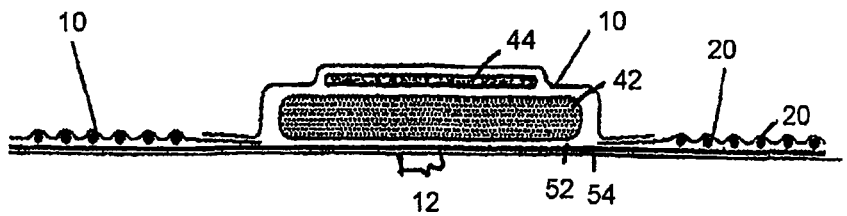
Figure 15:
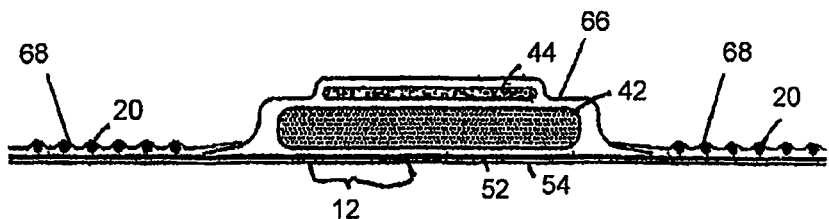
Figure 16:
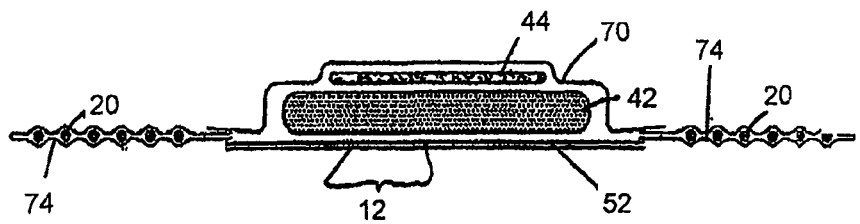
Figure 17:
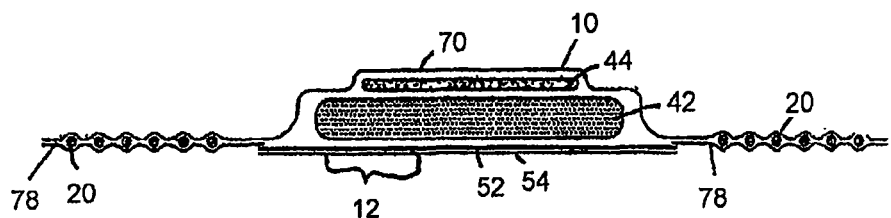
Figure 18:
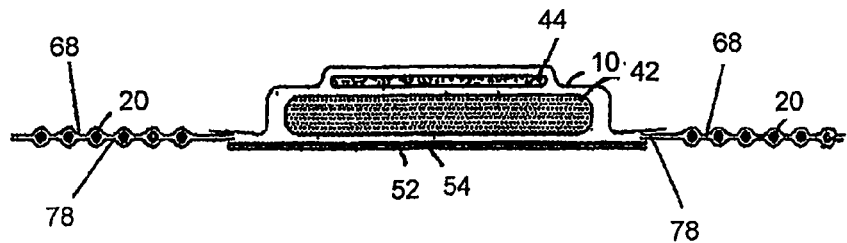
Figure 19:
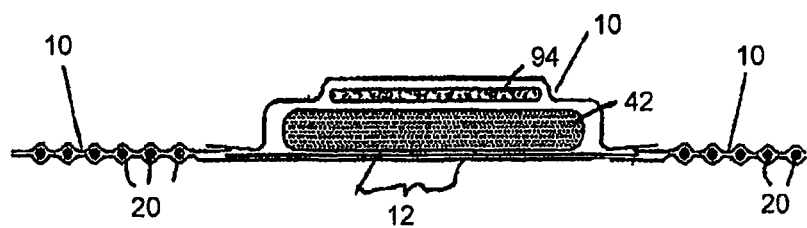
Figure 20:
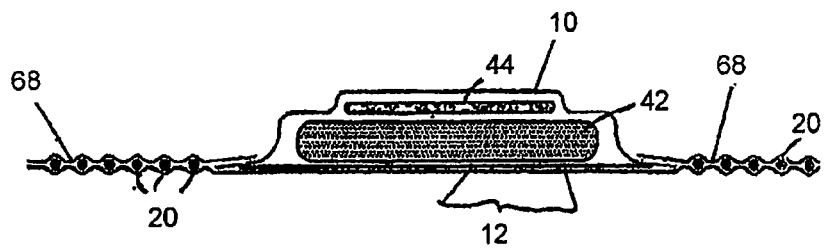
Figure 21:
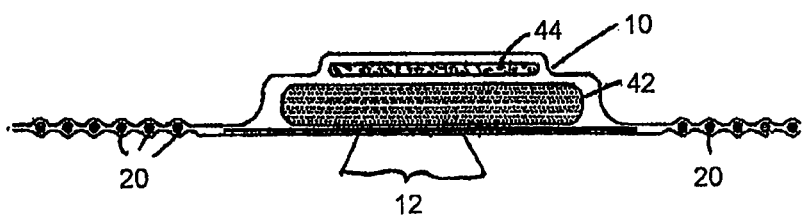

FIG. 13 shows an alternate embodiment to that shown in FIG. 11. This embodiment differs in that two separate layers of suitable material are used to enclose the elastic strand elements 20 within elastic composite elements which are affixed between the coverstock and backsheet portions of the core assembly 14.

FIGS. 14-24 show still further embodiments where the underside of the elastic composite side panels are formed from a material such as the fluid impermeable polypropylene nonwoven which extends continuously across the full width of the absorbent article.

FIGS. 25-28 depict a disposable absorbent article as fitted to the wearer. The novel internal topsheet 19 is shown in these figures. The absorbent article 8 folds inwards at point 80 and outwards at point 82. The absorbent article 8 may naturally conform to the shape depicted in FIGS. 25-28. It may be necessary or useful to prefix the article in this configuration by applying spots of adhesive or by using any other suitable means to ensure that the article is fitted correctly to the wearer.

The outcome of this folding pattern of the article is two fold. First, the elastic leg wraps 18 are desirably positioned against the wearer's body and fit securely around the upper thighs and buttocks of the user. This serves to create a generally fluid impermeable seal around the legs, crotch and thighs of the user, which reduces the incidence of leakage. Second, the absorbent core assembly 14 is held away from the body of the wearer, particularly in the crotch area of the article. This serves to create a void space 84 between the user's body and the absorbent core assembly 14.

Figure 26:
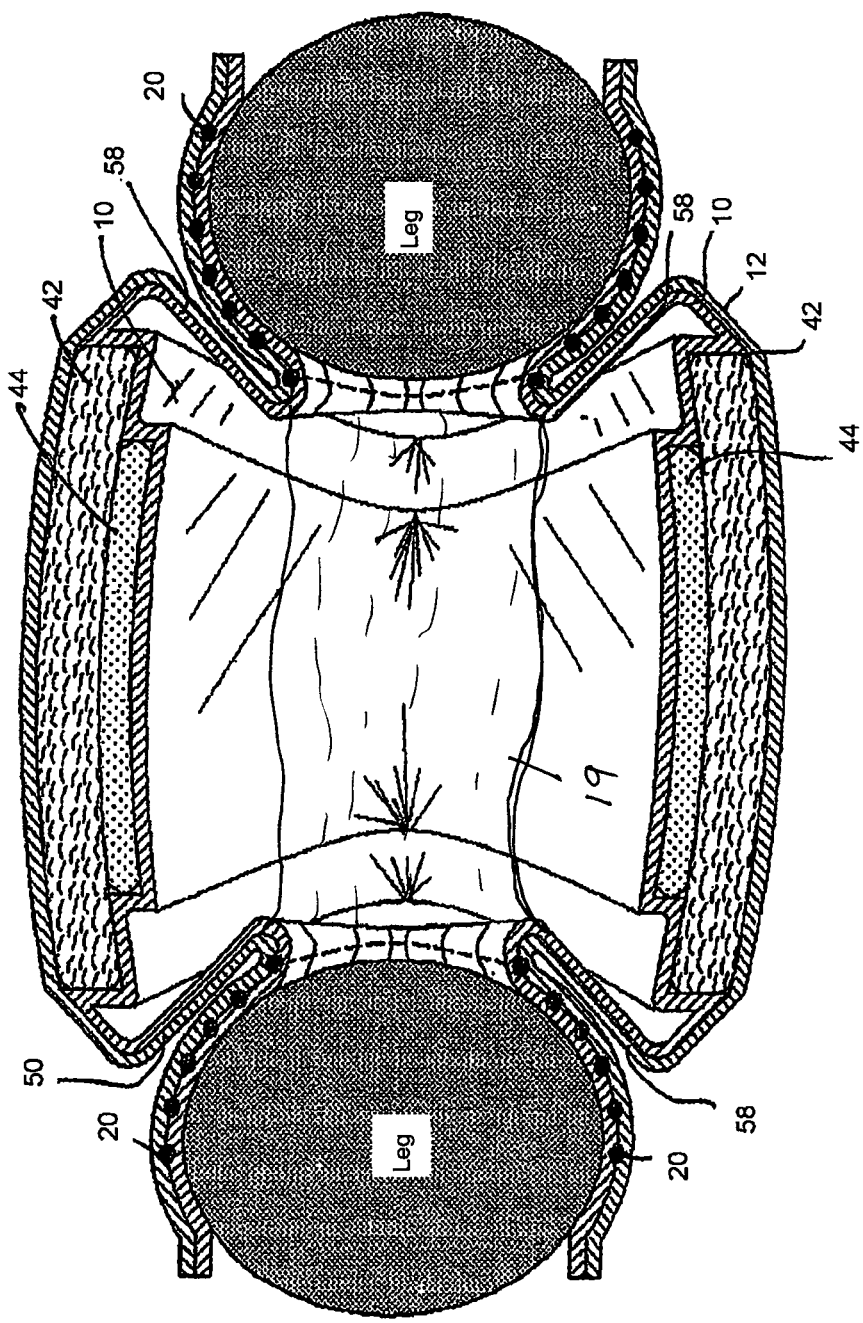
FIGS. 26 and 27 are depictions of cross-sections taken through an absorbent article and wearer.
Figure 27:
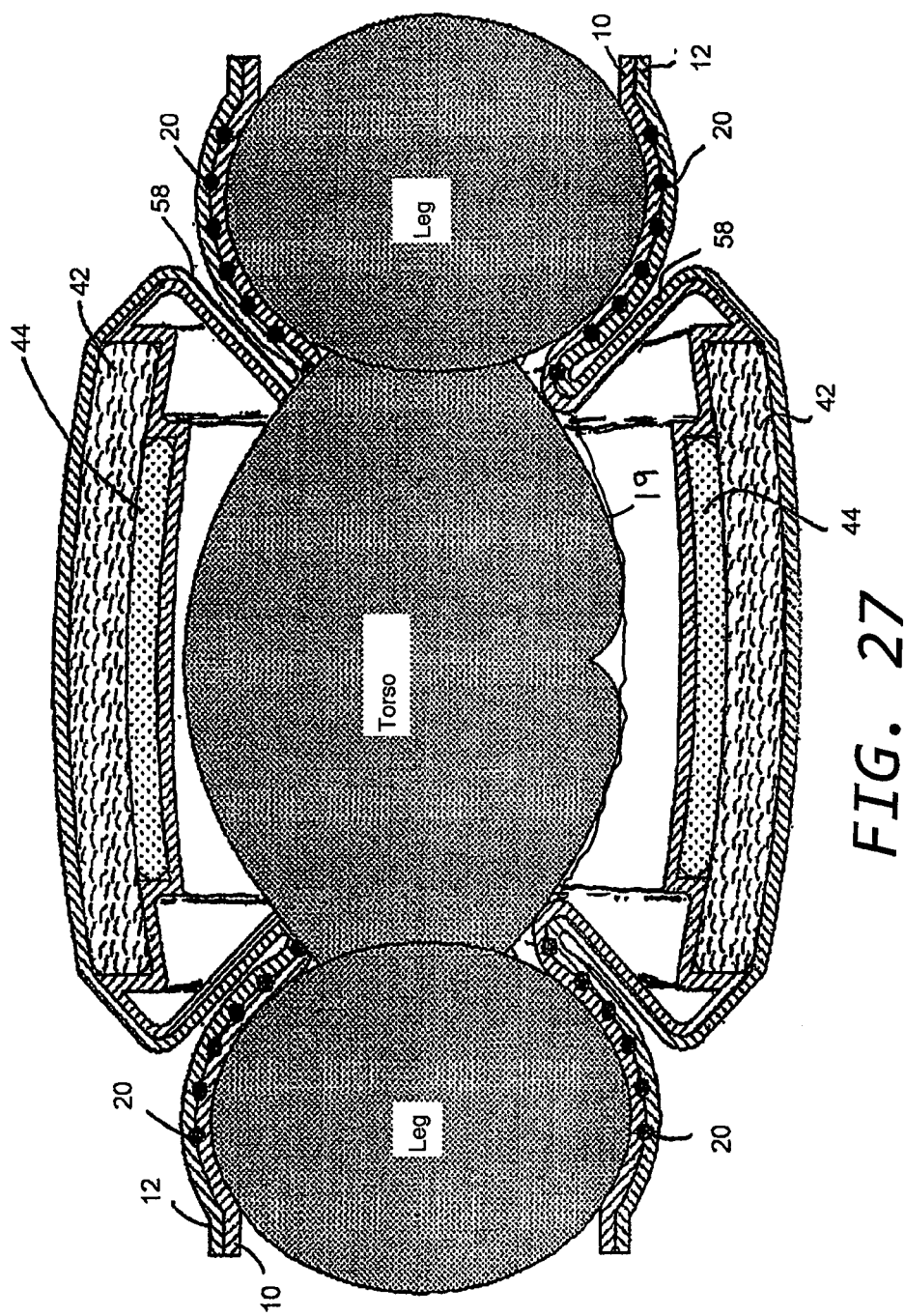

This void space 84 may have an approximately trapezoid appearance as demonstrated in FIG. 26, with a base having a length approximately equal to the width of the absorbent core 42, sides of a length approximately equal to dimension X, and a top length dependent upon the angle formed between the base and sides. Portions of the article 8 can pivot or rotate relative to each other so that the absorbent core 42 and leg wraps 18 can freely move upon the wearer. This pivoting effect enables the leg wraps 18 to move during use while maintaining an effective leg seal.

Void space 84 created by the structure of the absorbent article 8 serves to hold the absorbent core 42 away from direct contact with the skin or body of the wearer. For example, rewet or the wetting of the user's skin by body waste fluids not completely captured by the superabsorbent materials within the absorbent core 42 is reduced, resulting in improved comfort for the wearer.

Figure 25:
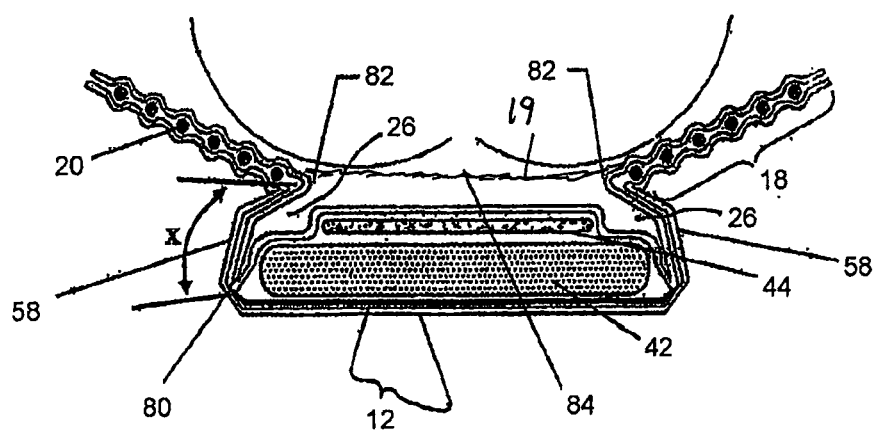
FIG. 25 is a depiction of the application of an absorbent article of the present invention upon a wearer.
Figure 22:
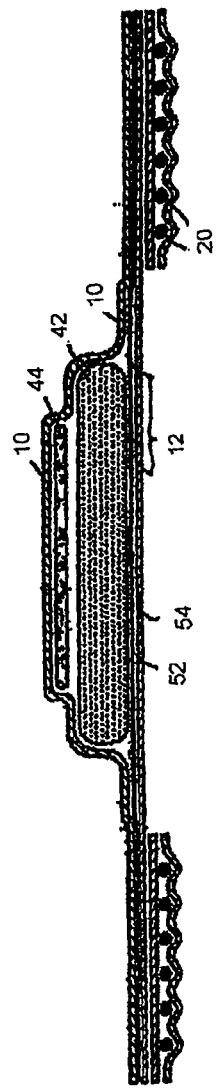
Figure 23:
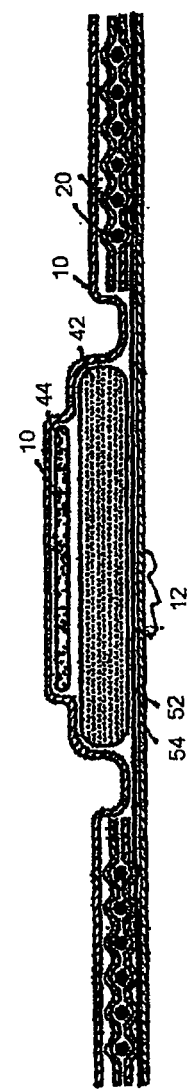
Figure 24:
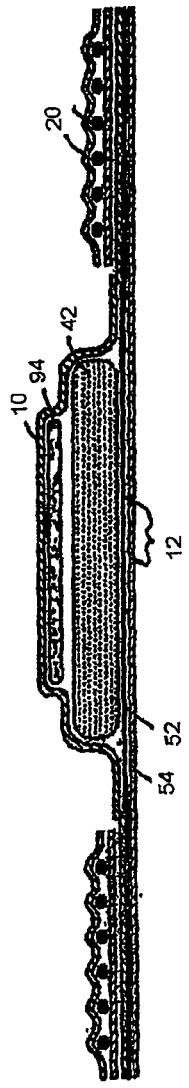

Referring particularly to FIGS. 25 and 28, reservoir 26 is a structure in which body exudates can be collected, contained and held. Exudates float or flow along the top surface flow into and down the side walls of the reservoir 26 to be collected in the bottom of the reservoir 26 until the absorbent article 8 can be removed. The reservoir 26 is, therefore, especially effective for exudates, particularly loose fecal materials, that are not easily absorbed by the absorbent core 14 and tend to "float" on the coverstock 10.

The reservoir 26 may be disposed at least in part between the elastic members 20 and the longitudinal centerline of the absorbent article 8, e.g., by material within the zone of decreased elasticity 58. The reservoir 26 may be constructed of materials known in the art which are compliant and conformable enough to present a pocket or well-like shape. The material may be absorbent, wicking or impermeable to exudates. For example, the reservoir 26 may comprise an element (i.e., the coverstock 10, the backsheet 12 or the leg wrap 18) or any combination of these elements or other elements of the absorbent article 8 configured or folded to present a reservoir. In addition, the reservoir 26 may have a variety of shapes and cross-sections provided that a pocket or well-like shape is formed to contain and hold the exudates. For example, the reservoir 26 may have a semi-circular, square or parabolic cross-section. Preferably, the reservoir 26 is formed by folding material within the zone of decreased elasticity 58 and securing the folded portion to portions of the coverstock 10 adjacent the absorbent core 14.

FIG. 28 illustrates the temporary reservoir 26 and void 84 wherein the reservoir 26 contains fluid prior to absorption by core 14. Fluid is prevented from passing through side leg panels 18 by the series of elastic gathers defining a plurality of fluid dams as indicated by numeral 90. Fluid which passes through one of the fluid dams 90 encounters the furtherly-outward fluid dam 90. As a result, multiple sealing structures are provided by the leg wraps 18.

It has been found that the desired trapezoid shape of void 84 and/or reservoir 26 can be difficult to form and maintain in every application as it can be dependent on how the absorbent article 8 is placed on the user and movements the user might make whilst wearing the diaper. In order to improve the likelihood that this shape exists in the product when the diaper is fitted to the wearer and to improve the stability of the desired shape during use it is possible to pre-fold the diaper in the side regions of the product, and fix the fold with the addition of a bonding element. This bonding element could be any combination of adhesive, thermo-bonding, ultrasonic bonding or any other suitable method of bonding plastic and nonwoven based materials. It is also envisaged that this fold-fixing bond point could also be obtained using a hook and loop engagement system or other non-permanent fixation means.

Figure 29:
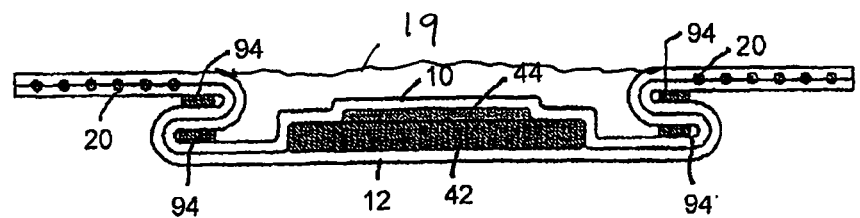
FIG. 29 is a cross-sectional view illustrating a folded side panel concept in accordance with the present invention.

In some embodiments of the present invention a z-shaped fold is formed in the leg wrap 18 of the diaper during manufacture. The leg wraps 18 can be folded in towards the core and a suitable bonding method is then used to fix this fold in position. Secondly, the side panel is then folded back away from the core. An optional bonding method can be used to fix this fold in position. FIG. 29 shows a cross-section of the folded diaper with the fold-fixing bonded areas indicated as numeral 94. Bonded areas 94 are optional and embodiments of the present invention may not necessarily include bonded areas 94. Similarly, other embodiments of the present invention may include one or more bonded areas 94.

Figure 30:
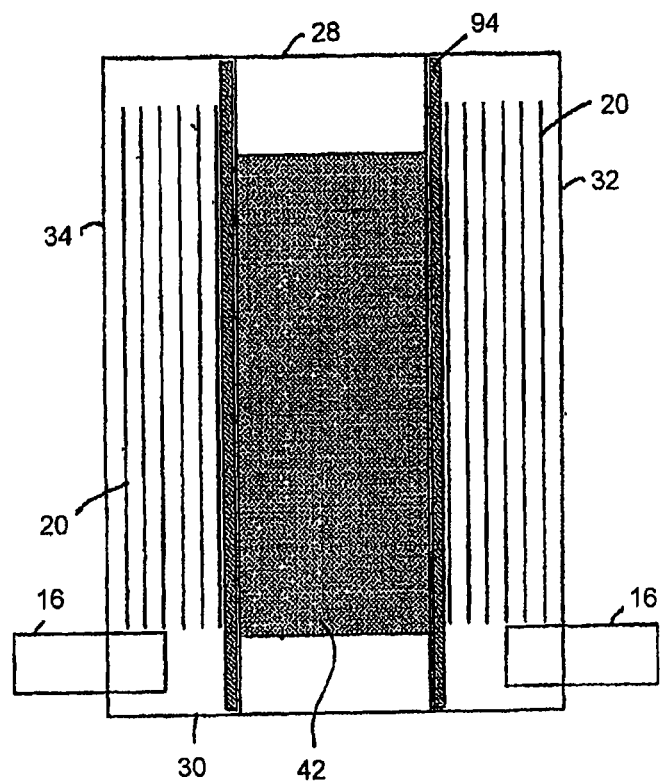
FIGS. 30-31 illustrate different embodiments of securing the folded side panel in accordance with the present invention.

Bonding of the folded side region can be achieved by a longitudinally continuous application of adhesive using any suitable application method, such as spiral spray, intermittent bead or continuous bead. Alternatively a continuous line of an ultrasonic or thermal bonding method could be used. FIG. 30 shows a diagram of this embodiment.

Figure 31:
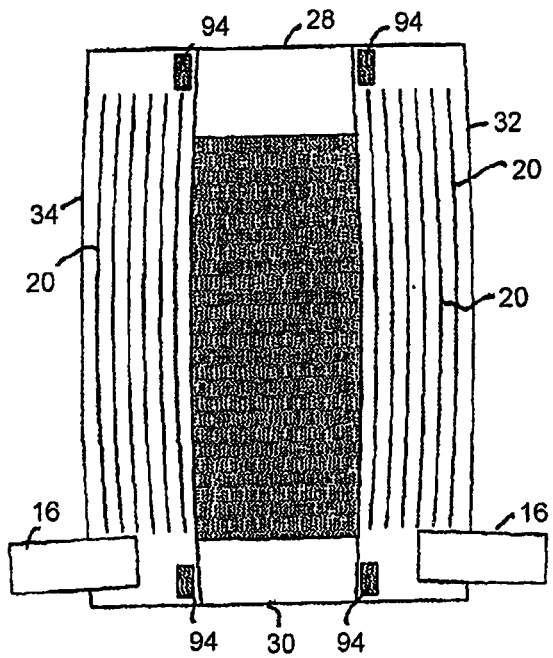
Figure 32:
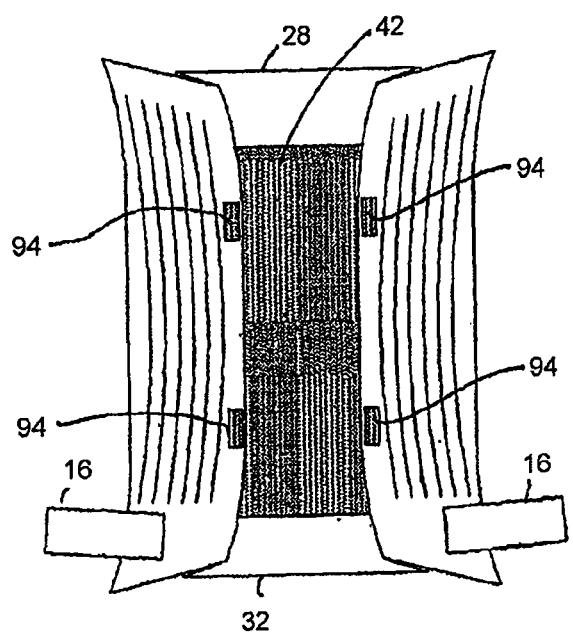
FIG. 32-36 are cross-sectional views illustrating the formation of a narrower topsheet gap relative to the backsheet gap in accordance with the present invention.
Figure 33:
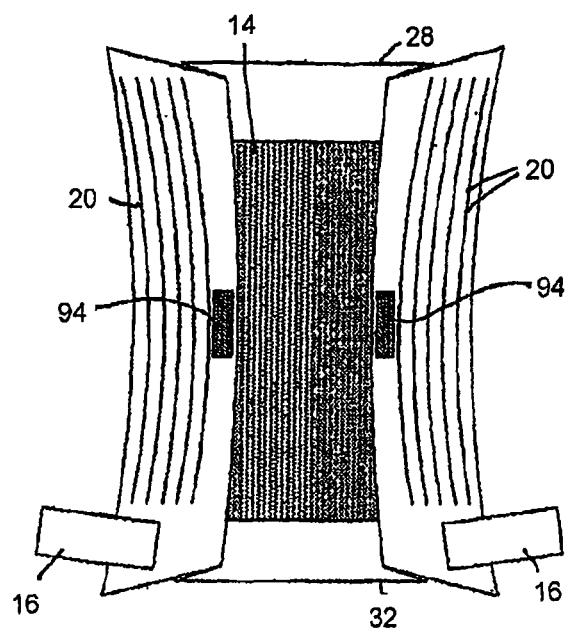

In further embodiments of this invention the longitudinal fold-fixing bonding points can be discontinuous. This has the advantage of allowing selection of zones on the diaper where the fold can open up to provide maximum void space, whilst effectively pinning the fold in position in other selected areas. In the embodiment of FIG. 31, two fold fixing bond points per side panel 18 are provided in a region close to the front and rear edges of the diaper. In another embodiment of FIG. 32 these bond points are moved towards the center of the diaper. In yet another embodiment of FIG. 33, a single bond point per side panel is provided in the center crotch region of the diaper.

The diagrams above show possible variations of the folded chassis of this invention and the possible positions for fold-fixing bond points. However further embodiments of this invention not shown by the drawings above are also possible. The position of the fold is variable and could be moved laterally to any position within the side panel or, alternatively, sections of the absorbent core could be incorporated into the folded region. The number of fold-fixing bond points per side panel is also variable.

Figure 34:
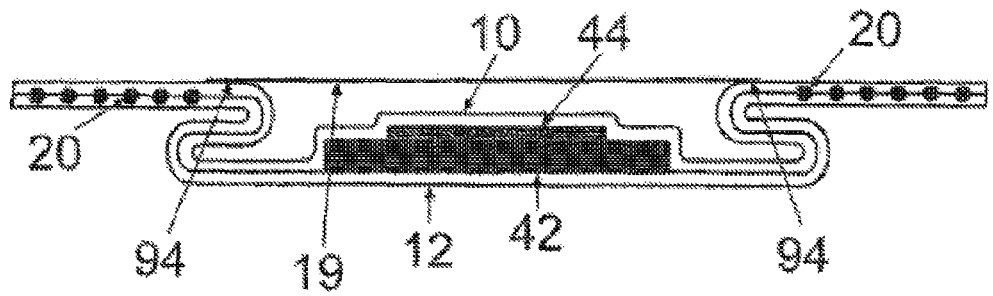
Figure 35:
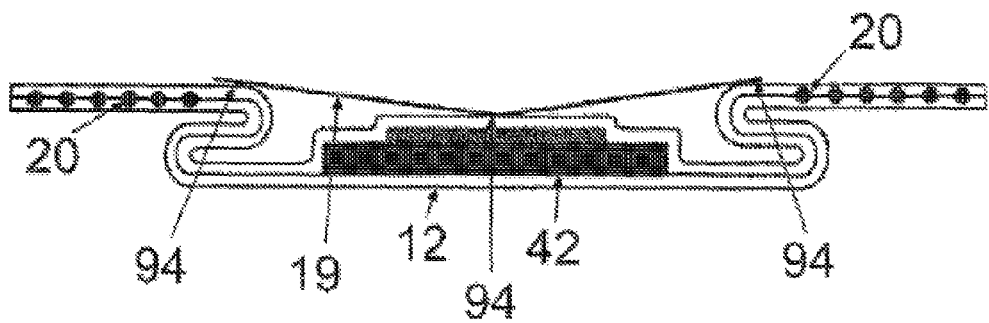
Figure 36:
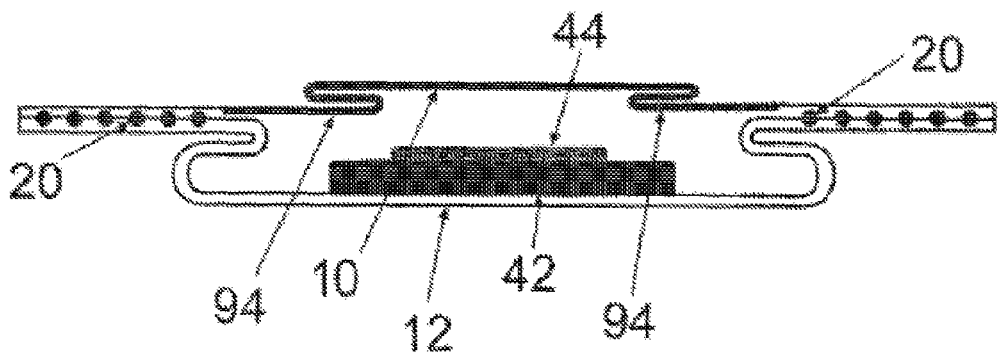
Figure 37:
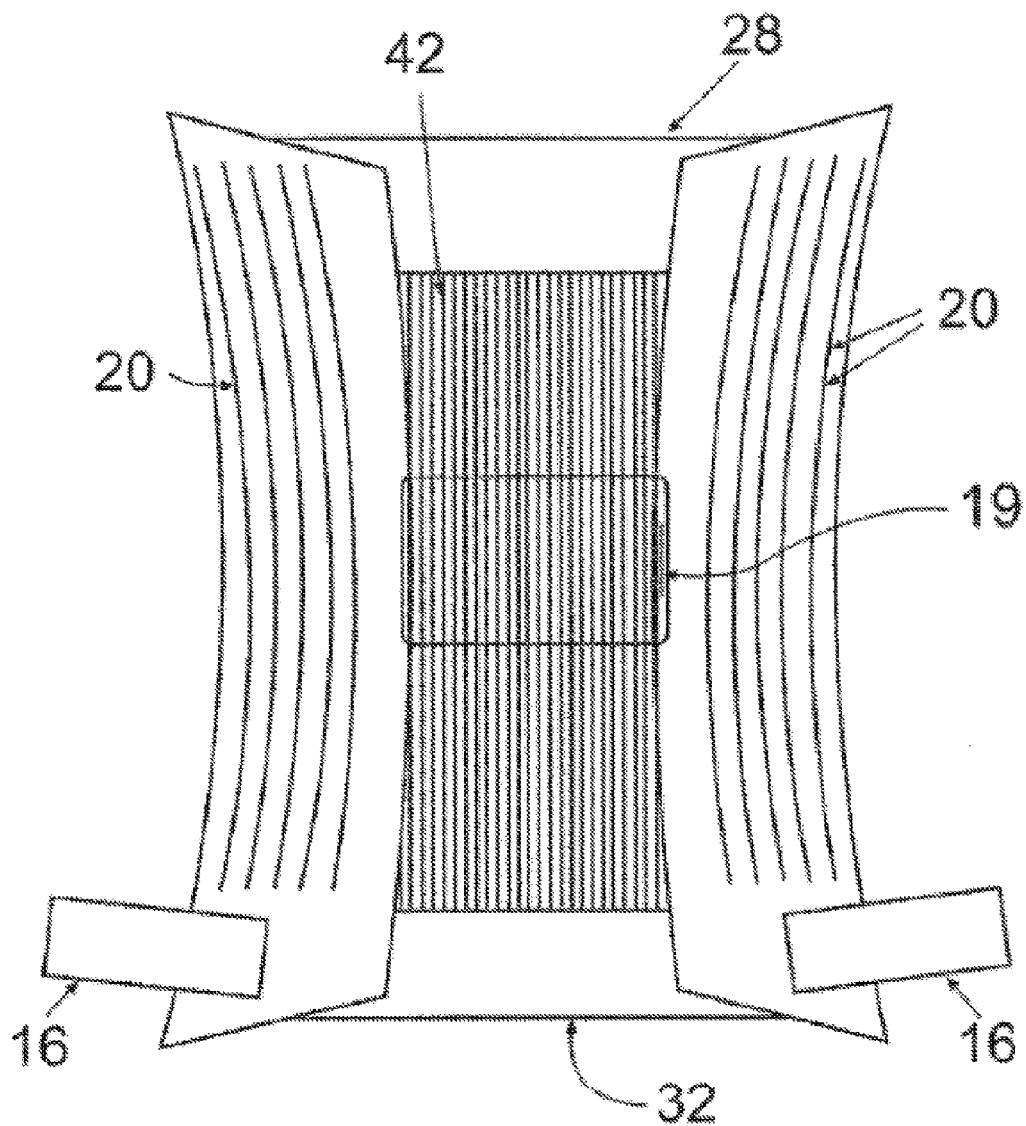
FIG. 37 illustrates a different embodiments of placing and attaching the topsheet in accordance with the present invention.

In addition to or in place of the use of the aforementioned fold-fixing bond points, providing a topsheet gap that is narrower than the back sheet gap can assure the maintenance of void 84 and/or reservoir 26. In a preferred embodiment illustrated in FIG. 34, secondary topsheet 19 ensures that the preferred void and/or reservoir is created and maintained even with variations in donning or fitting of the absorbent garment. The secondary topsheet 19 may also be additionally bonded to the absorbent as illustrated in FIG. 35. In another embodiment shown in FIG. 36, the primary topsheet 10 can be folded and bonded to itself to create the void and/or reservoir. FIG. 37 shows a partial length secondary topsheet 19 placed about the center of the diaper. Further embodiments not shown by the drawings are also possible. The positioning of the partial length topsheet 19 can be optimized for best performance in relation to the containment of fecal exudates and its separation from the skin. A plurality of topsheets 19 can also be envisioned and optimally positioned for best performance in fecal exudates handling. Additionally, topsheet 19 can have slits or holes to assist in the capture of liquid and solid exudates.

It is important that the tension forces provided by the elasticized side leg panel 18 are neither too low nor too high. If the tension forces provided by the side leg panel 18 are too low, the absorbent article 8 may not fit very closely in certain regions around the legs and the waist and the absorbent article ability to prevent leakage will be compromised. High tension forces may constrict the user's thighs and cause discomfort. In a typical prior art disposable absorbent article, the positioning of elastomeric elements and the type of elastomeric element placed does not vary along the length of the stretch panel. The elasticity or elastication of the stretch panel is, therefore, uniform along the stretch panel length. When elongated in a uniform manner, the overall tension provided by the stretch panel is also uniform along its length. The magnitude of this uniform tension depends on the overall elongation of the leg wraps 18. When the absorbent article 8 is worn, however, the elongation of the leg wrap 18 along it length is generally non-uniform, and thus, the tension generated varies. As a result, there may be regions about the length of the leg wrap 18 that are undesirably too loose or too tight.

In one respect, regions or zones devoid of elastic elements—e.g., zones provided for finger lift area and landing area—are also distinct regions of elasticity formed by pre-determined placement of elastic elements. These regions of elasticity differ, however, in the sense that the elastic elements do not impart elasticity to the stretch panel in these regions in contrast to the distinct regions of imparted elasticity in the vicinity of the elastic elements. Descriptions of some configurations suitable for use with the present invention are found in U.S. Ser. No. 10/441,469, entitled "Disposable Absorbent Article With Elasticized Side Panels and Method of Making Same", hereby incorporated by reference and made a part of the present disclosure.

In addition, embodiments of the absorbent article 8 achieve increased comfort by positioning the elasticized side flaps closer to the side edge of the absorbent core 42. Thus, when initially placed on the wearer, the elasticized side flaps ride in the groin areas along the inner thighs of the wearer thereby providing a better initial fit. This positioning provides a better initial fit on the wearer because elasticized side flaps of conventional diapers are often initially positioned farther down on the thigh of the wearer and subsequently tend to ride or creep up into the groin regions of the wearer during use. Because the side flaps are drawn up, gaps tend to form in the legs and waist providing less comfort for the wearer. However, because the present invention initially positions the elasticized leg wraps 18 in the groin areas, sagging of the diaper is reduced resulting in increased comfort for the wearer.

The foregoing description of the present invention has been presented for purposes of illustration and description. It is to be noted that the description is not intended to limit the invention to the various apparatus and processes disclosed herein. Various aspects of the invention as described above, may be applicable to other types of disposable absorbent articles and garments, and processes for making the same. For example, the feature of an elasticized side panel having the fastening portion described above, may be incorporated in other disposable absorbent articles such as training pants, etc. Moreover, the feature of an elasticized side panel as having the characteristic elasticity described above may also be incorporated in other disposable absorbent articles and garments. Such variations of the invention will become apparent to one skilled in the relevant consumer products, or other relevant art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

The invention claimed is:

1. A disposable absorbent article comprising:
a central body including an absorbent core, and a front end edge and a rear end edge spaced longitudinally from the front end edge, said end edges defining, at least partially, a front waist portion and a rear waist portion spaced longitudinally from the front waist portion, wherein the absorbent core extends longitudinally between the front waist portion and the rear waist portion and through a lateral centerline of the article that is spaced longitudinally from each of the front waist portion and the rear waist portion, and wherein a longitudinal centerline of the article extends longitudinally through the absorbent core and through the end edges bisecting the lateral centerline;
first liquid pervious topsheet,
wherein said absorbent core is disposed between the first liquid pervious topsheet and a liquid impervious backsheet;
a second topsheet extending across a second topsheet gap that is narrower than a backsheet gap wherein a difference between the second topsheet gap and the backsheet gap results in formation of a reservoir between the absorbent core and a wearer, the reservoir adapted to capture bodily exudates, wherein at least a portion of the reservoir is disposed between the first liquid pervious topsheet and the second topsheet; and
a pair of flexible leg wraps extending outwardly from and alongside edges of the absorbent core, the leg wraps each including a plurality of spaced-apart elastic strands separated from the absorbent core by an inelastic zone, wherein the leg wraps and the absorbent core form the reservoir and a plurality of fluid dams are defined at least in part by the plurality of elastic strands during use of the absorbent article, with each fluid dam capable of capturing a volume of liquid waste from passing between the leg wrap and the wearer; and
wherein said second topsheet spans laterally between said leg wraps and across said reservoir, said second topsheet being spaced above said first topsheet and said absorbent core, wherein a void is provided above said absorbent core between said first topsheet and said second topsheet; and
wherein said first topsheet is disposed between said second topsheet and said absorbent core and said reservoir is disposed above said first topsheet; and
wherein the lateral centerline of the article extends laterally through the flexible leg wraps, the second top sheet extending a longitudinal length from the lateral centerline toward the front waist portion and a longitudinal length toward the rear waist portion, and the second topsheet being disposed over a central part of the absorbent core that is spaced longitudinally from the waist portions and disposed about the lateral centerline.

2. The absorbent article of claim 1, wherein with the absorbent article disposed in a generally flat, open condition, the distance between the absorbent core and the nearest strand of elastic is between 19 mm to 64 mm, the number of elastic strands per inelastic zone is between 4 and 10 strands, and the distance between individual elastic strands is between 6 mm to 8 mm.

3. The absorbent article of claim 1, wherein said second topsheet spans laterally between said leg wraps and across said reservoir and longitudinally across the central part of the absorbent core between opposite waist end regions of the article.

4. The absorbent article of claim 1, wherein the inelastic zone is folded over to define portions of the reservoir.

5. The absorbent article of claim 4, wherein portions of the inelastic zone are adhered together in one or more locations of the absorbent article.

6. The absorbent article of claim 1, wherein said second topsheet extends from said front waist portion to said rear waist portion.

7. The absorbent article of claim 1, wherein at least the first liquid pervious topsheet has zones of differing hydrophilic properties.

8. The absorbent article of claim 6, wherein the elastic strands are provided with a plurality of different diameters.

9. A disposable absorbent article comprising:
a central body including an absorbent core, and a front end edge and a rear end edge spaced longitudinally from the front end edge, said end edges defining, at least partially, a front waist portion and a rear waist portion spaced longitudinally from the front waist portion, wherein the absorbent core extends longitudinally from the front waist portion to the rear waist portion and through a lateral centerline of the article that is spaced longitudinally inward from each of the front waist portion and the rear waist portion, and wherein a longitudinal centerline of the article extends longitudinally through the absorbent core and through the end edges bisecting the lateral centerline;

first liquid pervious topsheet, an absorbent core disposed between the first liquid pervious topsheet and a liquid impervious backsheet, the absorbent core extending longitudinally between waist end regions of the article;

a second topsheet extending across a second topsheet gap that is narrower than a backsheet gap wherein a difference between the topsheet gap and the backsheet gap results in formation of a reservoir between the absorbent core and a wearer that is capable of capturing bodily exudates, wherein at least a portion the reservoir is disposed between the first liquid pervious topsheet and the second topsheet; and a pair of elasticized leg wraps extending longitudinally adjacent opposite lateral sides of the absorbent core, the leg wraps including a plurality of spaced-apart elastic strands, wherein the reservoir is defined between the absorbent core and folded portions of the leg wrap during use, and a plurality of fluid dams are defined in part by the plurality of spaced-apart elastic strands during use, with each of the plurality of fluid dams capable of retaining a fluid volume against leakage from the leg wraps; and wherein said second topsheet is joined to said leg wraps and spans laterally between said leg wraps and across said reservoir and longitudinally along a longitudinal length of the absorbent core, and wherein a void is provided spaced below said second topsheet and above said absorbent core; and wherein said second top sheet extends over the absorbent core from the front waist portion to the rear waist portion, and over a central part of the absorbent core spaced longitudinally inward from the front and rear waist portions.

10. The absorbent article of claim 9, wherein with the absorbent article provided in a generally flat, opened orientation, the distance between the absorbent core and the nearest strand of elastic is between 25 mm to 51 mm, the number of elastic strands is between 5 and 10, and the distance between the individual strands is between 5 mm to 10 mm.

11. The absorbent article of claim 9, wherein the number of elastic strands is between 6 and 8 strands.

12. The absorbent article of claim 9, wherein the distance between the individual strands is between 6 mm to 9 mm.

13. The absorbent article of claim 9, wherein the distance between the absorbent core and the nearest elastic strand is between 10 mm to 100 mm.

14. The absorbent article of claim 1, wherein each flexible leg wrap includes a folded portion forming, at least partly, said reservoir; and wherein said second topsheet bonds to each leg wrap at a bonded area on the folded portion and spans laterally therefrom between said leg wraps.

15. The absorbent article of claim 9, wherein the second topsheet is positioned above the absorbent core and wherein the void is formed between the leg wraps and below the second topsheet.

16. The absorbent article of claim 15, wherein said second topsheet is joined to each leg wrap and spans laterally therefrom across said reservoir, said second topsheet being spaced above said first topsheet and said absorbent core, and wherein said first topsheet is disposed between said second topsheet and said absorbent core and said reservoir is disposed above said first topsheet.

17. The absorbent article of claim 9, wherein each flexible leg wrap includes a folded portion forming, at least partly, said reservoir; and wherein said second topsheet bonds to each leg wrap at a bonded area on the folded portion and spans laterally therefrom between said leg wraps.

18. The absorbent article of claim 1, wherein said second topsheet and said absorbent core each extends from the front waist portion to the rear waist portion, and each of said front and rear waist portions having a length less than one-quarter of a length of the absorbent article from the front end edge to the rear end edge.

19. The absorbent article of claim 9, wherein said central part of the absorbent core is disposed about said lateral centerline from one leg wrap to the other leg wrap and extends therefrom in one direction toward the front waist portion and in opposite direction toward the rear waist portion.

20. The absorbent article of claim 1, wherein the second topsheet is attached to each of the flexible leg wraps, extending from one flexible leg wrap to the other flexible leg wrap, wherein each flexible leg wrap is spaced outwardly from a lateral edge of the absorbent core, and wherein the void extends from one flexible leg wrap to the other flexible leg wrap.

21. The absorbent article of claim 1, wherein the reservoir is defined at least partially by the second topsheet and a portion of each of the pair of flexible leg wraps.

22. The absorbent article of claim 1, wherein the reservoir is defined between the absorbent core and folded portions of the flexible leg wrap during use of the absorbent article.

23. The absorbent article of claim 1, wherein the second topsheet is a discrete element attached to the flexible leg wraps above the absorbent core, and wherein the reservoir is defined at least partially by the second topsheet and a portion of each of the pair of flexible leg wraps.

* * * * *